United States Patent [19]

Adair

[11] Patent Number: 5,591,119
[45] Date of Patent: Jan. 7, 1997

[54] STERILE SURGICAL COUPLER AND DRAPE

[76] Inventor: Edwin L. Adair, 317 Paragon Way, Castle Pines Village, Colo. 80104

[21] Appl. No.: 350,682

[22] Filed: Dec. 7, 1994

[51] Int. Cl.⁶ ........................................................ A61B 1/04
[52] U.S. Cl. ............................ 600/112; 600/122; 396/17
[58] Field of Search .................................. 600/112, 121, 600/122, 124; 128/849, 851, 853, 855, 856; 359/510, 511; 354/62; 604/163

[56] References Cited

U.S. PATENT DOCUMENTS

| | | | |
|---|---|---|---|
| Re. 34,002 | 7/1992 | Adair | 358/229 |
| 2,132,549 | 10/1938 | Wenstrom | 95/22 |
| 2,537,303 | 1/1951 | Cobb, Jr. et al. | 95/11 |
| 3,026,784 | 3/1962 | Byers | 95/11 |
| 3,821,759 | 6/1974 | Vooght | 95/11 UW |
| 4,522,196 | 6/1985 | Cunningham et al. | 600/112 |
| 5,078,483 | 1/1992 | Herzberg | 85/38 |
| 5,198,894 | 3/1993 | Hicks | 358/98 |
| 5,239,981 | 8/1993 | Anapliotis | 128/4 |
| 5,274,500 | 12/1993 | Dunn | 359/507 |
| 5,325,846 | 7/1994 | Szabo | 128/4 |

FOREIGN PATENT DOCUMENTS

| | | | |
|---|---|---|---|
| 8914215.2 | 2/1991 | Germany . | |
| 2223681 | 4/1990 | United Kingdom | 604/163 |

*Primary Examiner*—Richard J. Apley
*Assistant Examiner*—Beverly M. Flanagan
*Attorney, Agent, or Firm*—Fields & Johnson, P.C.

[57] ABSTRACT

An apparatus and method is provided for enclosing a non-sterile video camera, its trailing cables, and a standard optical connector such as a "C" mount for use of the camera in the sterile environment of an operating room. The apparatus includes a coupler having a first end for attachment to the unsterile optical connector and a second end for attachment to a sterile endoscope. A passageway is formed inside the coupler that extends from the first end to the second end providing an optical pathway whereby an image from the endoscope may be transmitted to the camera. A transparent window is mounted transversely across the passageway between the first and second ends of the coupler which provides a sterile barrier therebetween. A sterile drape is positioned over the first end of the coupler and is secured to a neck portion that joins the first and second ends of the coupler. The sterile drape is secured such that a fluid and airtight seal is formed between the ends of the coupler. Typically, the seal is formed by surgical tape or adhesive.

14 Claims, 5 Drawing Sheets

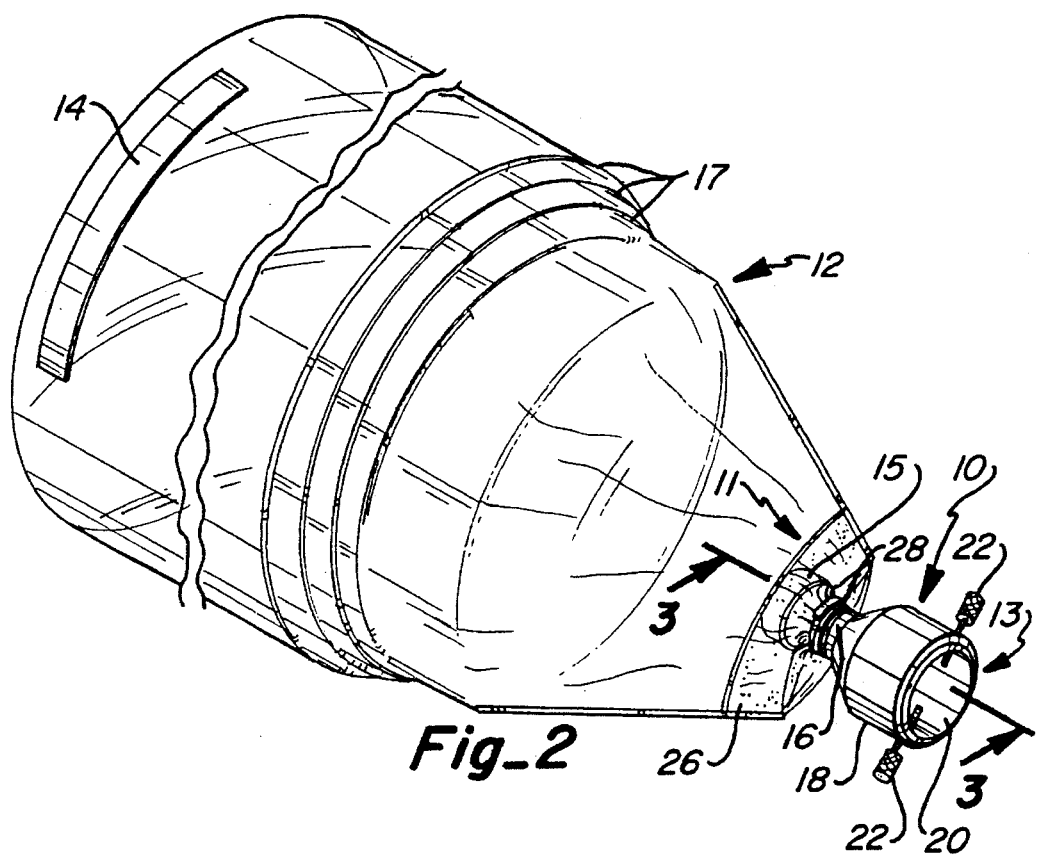
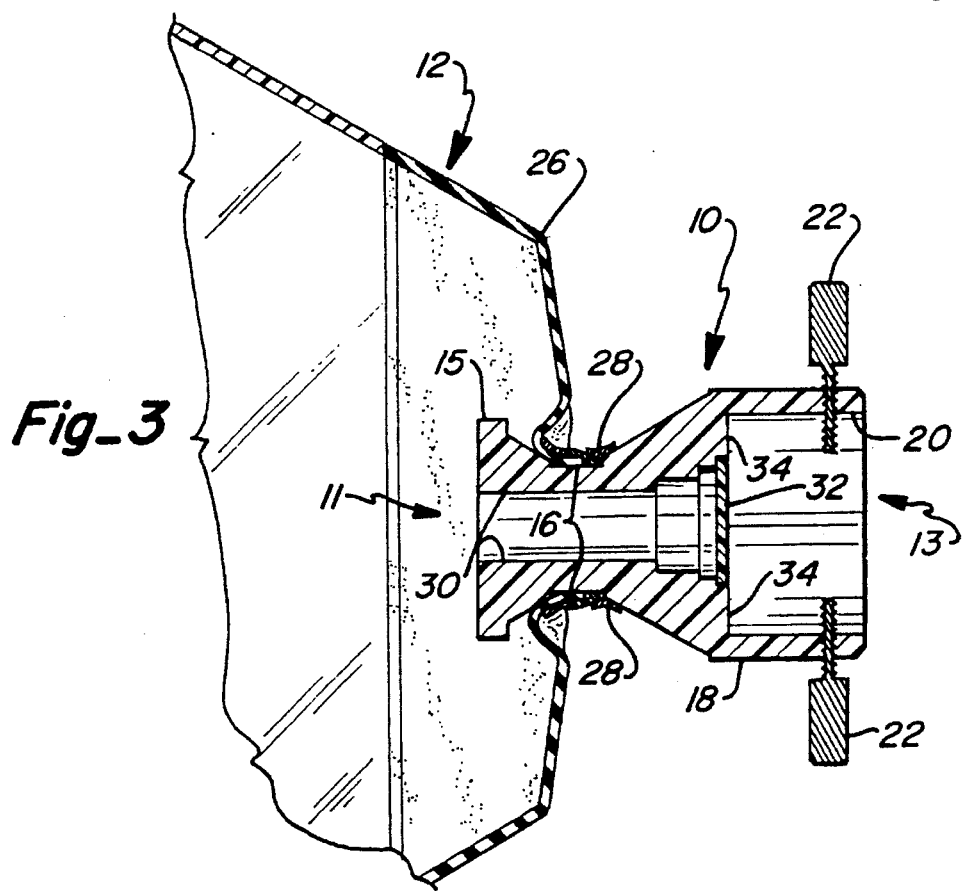

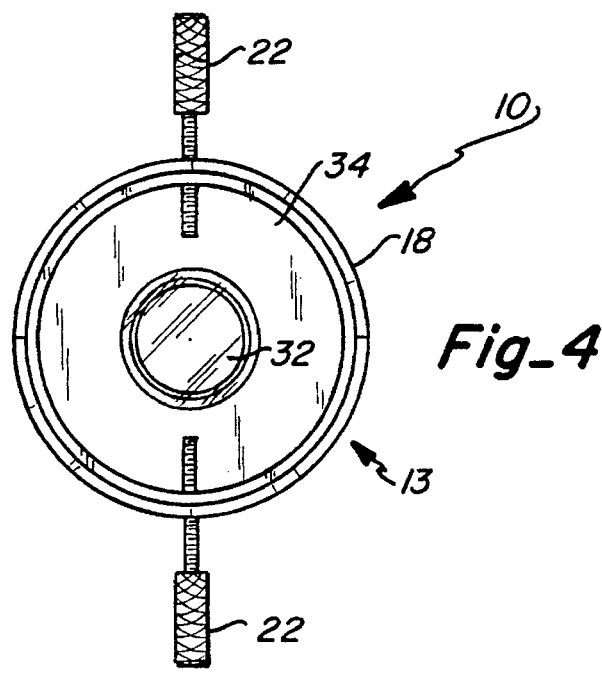
Fig_4
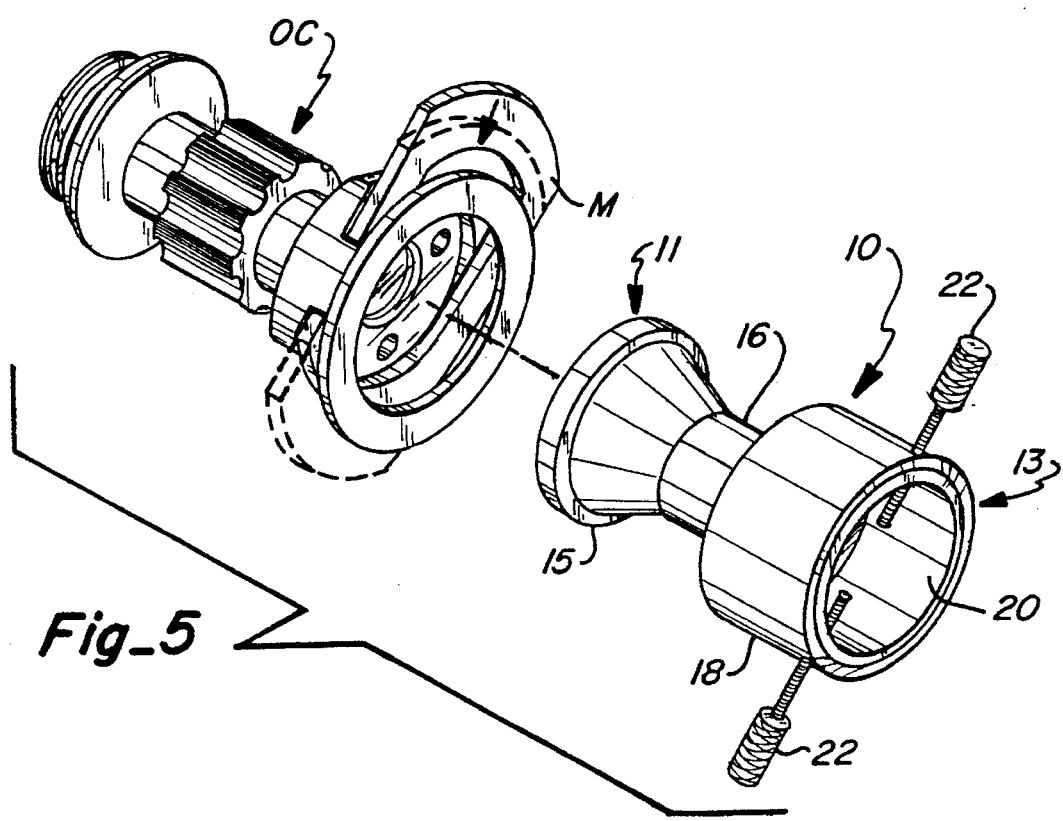
Fig_5

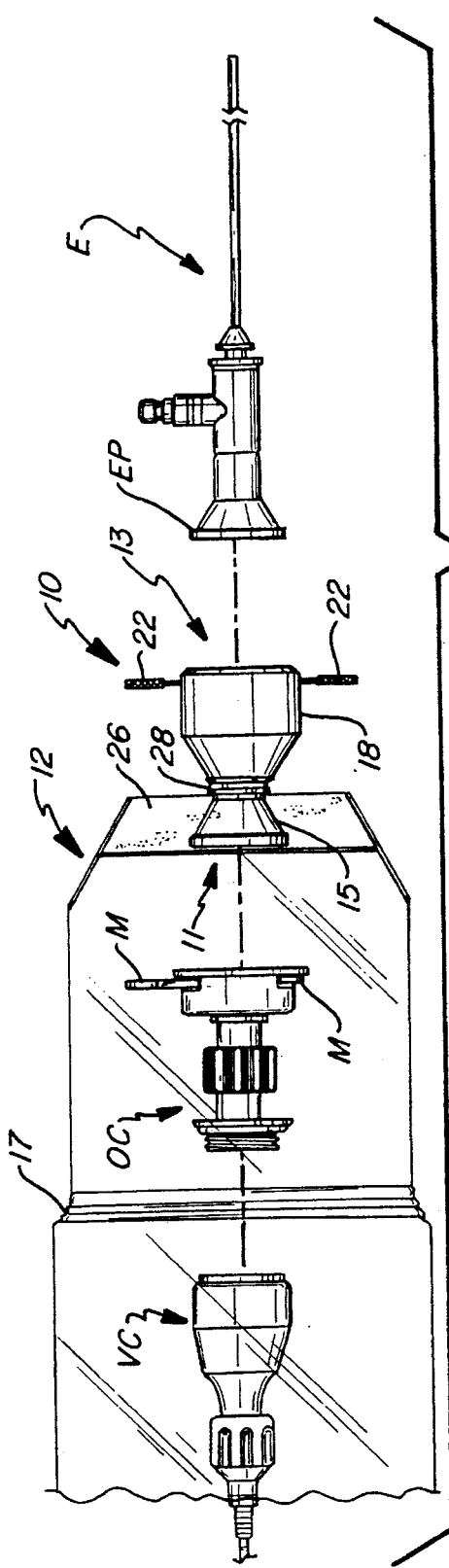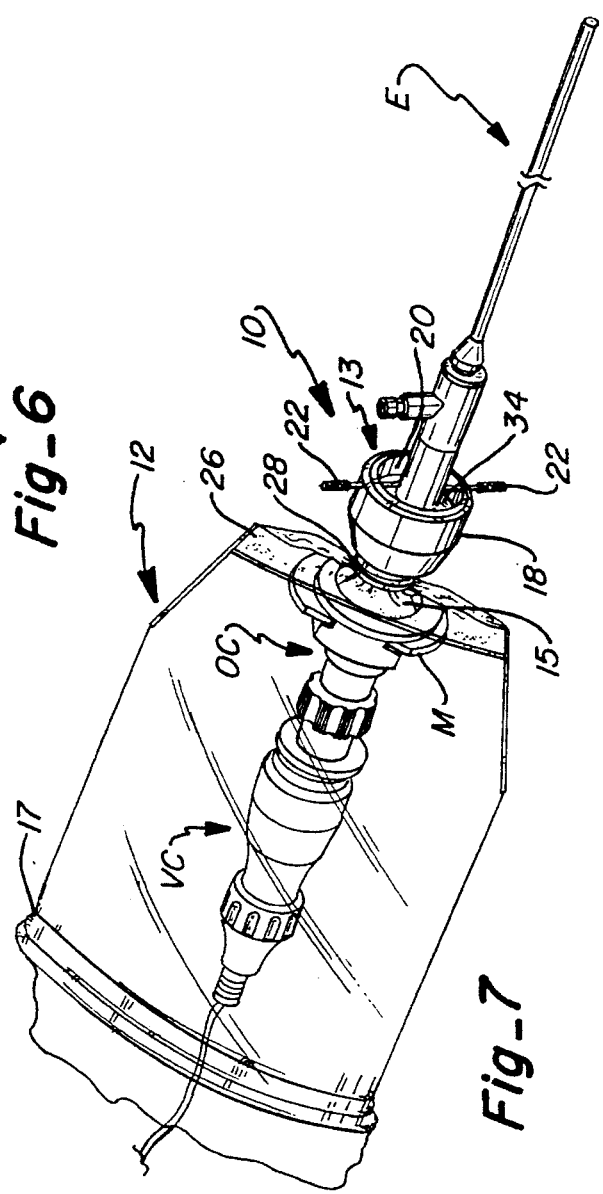

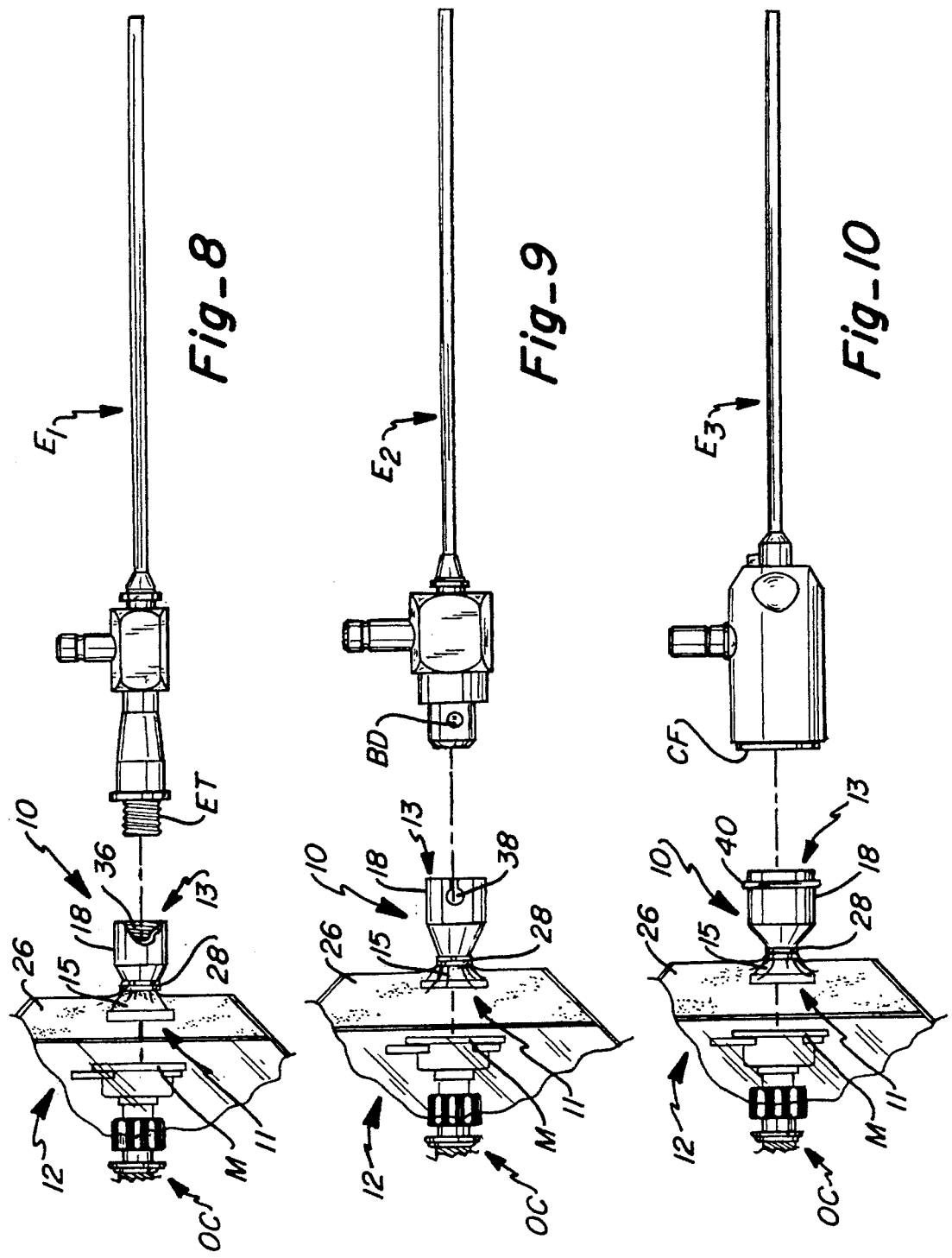

5,591,119

STERILE SURGICAL COUPLER AND DRAPE

TECHNICAL FIELD

This invention relates to a sterile surgical coupler and drape for use in the sterile environment of an operating room. More particularly, the invention relates to such a coupler and drape which encloses an unsterile camera setup including a camera and an optical connector wherein the unsterile optical connector attaches to a first end of the coupler and a second end of the coupler in turn attaches to a sterile endoscope.

BACKGROUND ART

For many years, unsterile surgical cameras and optical connectors known in the art as "C" or "V" mount connectors have been used in surgery by placing them into a sterile plastic bag or drape that has a distal end including an opening for receiving the eyepiece of a sterile or disinfected endoscope. The act of coupling the sterile or disinfected endoscope through the opening in the drape to the unsterile optical connector can create contamination. That is, the interior of the drape that houses the unsterile camera and optical connector is exposed to the sterile environment of an operating room through the hole located at the distal end of the drape. When the eyepiece of the endoscope is inserted through this hole for connection to the optical connector, this hole often becomes enlarged thus enhancing the possibility of contamination travelling from the interior of the drape to the sterile operating room. The further acts of aligning the endoscope with the optical connector and sealing the distal end of the drape around the protruding distal portion of the endoscope can also result in further contamination.

My earlier U.S. Pat. No. Re. 34,002 discloses a sterilizable video camera cover which has a connector including a guideway for receiving an unsterile video camera within it in a predetermined fixed orientation. One end of the video camera cover receives a sterile mount and endoscope in a fixed position with respect to the camera. An accordion-folded sleeve is positioned on the camera cover and is extended over the trailing cables of the camera to maintain the sterile environment within the operating room even though the camera and trailing cables are unsterile.

A sterile pouch for containing a standard still picture camera for use in an operating room is shown in U.S. Pat. No. 2,537,303 to Cobb, Jr. et al. However, there is no thought in this device of connecting the camera to other optical means. Other containers for protecting cameras in varying environments are shown in U.S. Pat. No. 3,026,784 to Byers, U.S. Pat. No. 3,821,759 to Vooght and U.S. Pat. No. 2,132,549 to Wenstrom. However, none of these references are intended for use in an operating room to maintain the environment within the operating room in a sterile condition when the camera is not sterile.

There are numerous references which disclose sterile drapes or covers for isolating an unsterile camera and its trailing cables from the sterile environment of an operating room. Examples of such references include U.S. Pat. No. 5,274,500 to Dunn, U.S. Pat. No. 5,078,483 to Herzberg, U.S. Pat. No. 5,198,894 to Hicks, and U.S. Pat. No. 5,325,846 to Szabo. While each of these references may be adequate for their intended purpose, none of these references disclose a device which allows endoscopes to be freely interchanged with a single camera setup and yet maintain the required sterility of an operating room.

DISCLOSURE OF THE INVENTION

An apparatus and method is provided for enclosing a non-sterile video camera, its trailing cables, and a standard optical connector such as a "C" mount connector for use of the camera in the sterile environment of an operating room. The apparatus includes a coupler having a first end for attachment to the unsterile optical connector and a second end for attachment to a sterile endoscope. A passageway is formed inside the coupler that extends from the first end to the second end providing an optical pathway whereby an image from the endoscope may be transmitted to the camera. A transparent window is mounted transversely across the passageway between the first and second ends of the coupler which provides a sterile barrier therebetween. A sterile drape is positioned over the first end of the coupler and is secured to a neck portion that joins the first and second ends of the coupler. The sterile drape is secured such that a fluid and airtight seal is formed between the ends of the coupler. Typically, the seal is formed by surgical tape or adhesive or both. The first end of the coupler includes a flared annular mounting that duplicates the eyepiece of a standard endoscope. This flared annular mounting is compatible with common optical connectors available from various manufacturers, including Olympus, Karl Storz and others. The second end of the coupler may include a number of embodiments which are intended to allow this end of the coupler to be attached to differing types of endoscopes. For example, in one embodiment, the second end of the coupler includes a cylindrical interior wall for receiving a standard endoscope with an annular eyepiece. Means are provided for securing the endoscope to the second end of the coupler, such as by retaining screws, pins, or other appropriate means. In another embodiment, the second end of the coupler may include an interior wall having threads which engage with an endoscope having an exterior threaded end instead of the conventional eyepiece. In another embodiment, the second end of the coupler may include a generally circular recess for receiving an endoscope of the type which has a spring-loaded ball detent. In yet another embodiment, the second end of the coupler may include an external O-ring for receiving an endoscope of the type having a compression fitting. The drape may be accordion folded or roll folded so to accommodate the desired packaging size prior to use. Conveniently, the drape may also include a pull tab for extending the drape for use. The coupler and drape are generally sterilized by gamma radiation or by gas sterilization and thus may be completely sterile.

Stated in another way in broader terms, the invention is a sterile system for coupling a sterile endoscope to an unsterile camera wherein endoscopes are freely interchangeable with the same camera setup so that sterility can be maintained. A coupling means is provided for coupling an unsterile optical connector to a sterile endoscope. The coupling means may be any suitable device having a first end for receiving the unsterile optical connector and a second end for receiving the sterile endoscope. A drape is provided wherein the first end of the coupler remains completely sealed from the sterile environment of the operating room while the second end of the coupler is exposed to the operating room and which allows one to attach the needed endoscope without having to access the optical connector or camera. The sterile drape completely encloses the camera, its trailing cables, and the optical connector.

Some cameras and optical connectors may be partially disinfected by soaking or heating, however, it is quite difficult to completely sterilize these pieces of equipment without incurring tremendous expense due to the cost of labor and equipment associated with surgical sterilization techniques. Thus, a preferred method of endoscopy is one in which unsterile cameras and accessories may be coupled to sterile endoscopes with operating room sterility maintained throughout. With the invention just described, it is possible to use a standard and unsterile surgical camera and a standard and unsterile optical connector such as a "C" mount connector with a multitude of different types of endoscopes. As described, sterility can be maintained throughout any acts of endoscope manipulation such as changing or adjusting an endoscope with the same camera setup.

Additional advantages of this invention will become apparent from the description which follows, taken in conjunction with the accompanying drawings.

BRIEF DESCRIPTION OF THE DRAWINGS

FIG. 2 is a perspective view of a sterile surgical coupler and drape constructed in accordance with this invention;

FIG. 3 is a longitudinal cross-sectional view taken along line 3—3 of FIG. 2 showing the interior details of the coupler and drape;

FIG. 4 is an end view of the preferred embodiment of the coupler illustrating the coupler having an internal optical pathway therethrough;

FIG. 5 is a perspective exploded view of the coupler detached from the drape and a standard optical connector, known in the art as a "C" mount or "V" mount connector, prior to engagement of the coupler with the optical connector;

FIG. 6 is an exploded side view of the surgical coupler and drape of this invention illustrating the alignment of a camera, optical connector and an endoscope prior to connection;

FIG. 7 is a perspective view of the sterile surgical coupler and drape of this invention illustrating the invention in use wherein an unsterile camera and optical connector are inserted within the drape and connected to the first end of the coupler, and a sterile endoscope is connected to the second end of the coupler;

FIG. 8 is a partial fragmentary exploded side view of the invention illustrating an alternative embodiment wherein the second end of the coupler has interior threads for receiving an endoscope of the type having an exterior threaded end;

FIG. 9 is an exploded side view of the invention illustrating another alternative embodiment wherein the second end of the coupler includes a generally circular recess for receiving an endoscope of the type having a spring-loaded ball detent connection; and FIG. 10 is an exploded side view of the invention illustrating yet another alternative embodiment wherein the second end of the coupler includes an external O-ring for receiving an endoscope of the type having a compression fitting connection.

BEST MODE FOR CARRYING OUT THE INVENTION

Figure 1:
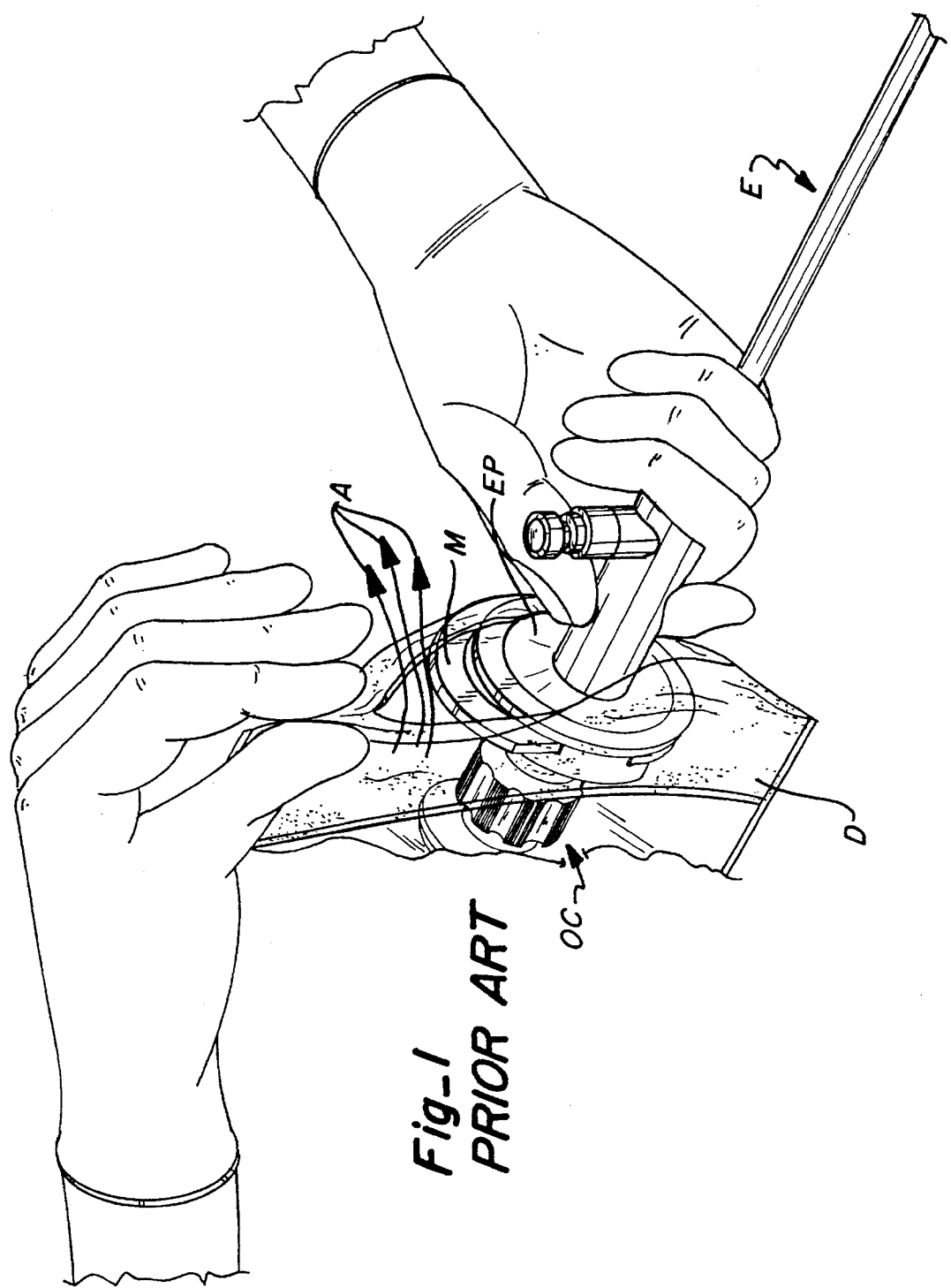
FIG. 1 is a perspective view of the prior art illustrating the eyepiece of a sterile endoscope being directly coupled to an unsterile optical connector wherein the eyepiece is inserted through an opening in the distal end of the drape.

Typically, a sterile endoscope is connected by means of an optical connector to a surgical camera. The distal end of the endoscope can be introduced into an internal body sight for viewing. The maintenance of sterility in these types of medical procedures is critical. While there does exist sterile cameras and optical connectors, it is more common in the art to encounter surgical cameras and optical connectors that are unsterile and that are shielded from the sterile environment of the operating room by means of a sterile drape or bag.

The invention disclosed herein is advantageous over the prior art because sterility can be maintained during endoscopic procedures. In the prior art method and device of FIG. 1, a standard endoscope E with eyepiece EP is inserted within drape D. The act of inserting the eyepiece EP into the drape D and coupling the eyepiece EP to an unsterile mount portion M of optical connector OC allows contamination to travel from the inside of the drape D to the sterile environment of the operating room. This path of contamination is generally shown by arrows A. Further contamination can occur by manipulation of the endoscope to achieve correct camera alignment and by sealing the open distal end of the drape to the protruding distal portion of the endoscope. Assuming the interior of the drape is sterile prior to the insertion of a camera and optical connector, the invention disclosed herein is still advantageous over the prior art. That is, sterility in the prior art can be maintained by first inserting the endoscope into the distal end of the drape and sealing the drape with respect to the endoscope prior to introducing the unsterile camera and optical connector into the drape. However, if it were desired then to change the type of endoscope used with the existing camera setup, the sterile barrier between the camera and the distal end of the endoscope would have to be broken by reopening the sealed end of the drape. This act can result in contamination and is therefore an undesirable method of interchanging endoscopes with the same camera setup. As will be discussed, the invention disclosed herein allows endoscopes to be freely interchanged and ensures the maintenance of sterility during endoscope procedures.

In accordance with this invention, a disposable sterile coupler 10 and attached sterile drape 12, as best seen in FIGS. 2 and 6, is provided for coupling an unsterile video camera VC and optical connector OC to a sterile endoscope E. The overall structure of the sterile coupler 10 and drape 12 can best be seen by viewing FIGS. 2 and 3. The sterile coupler 10 includes a first end 11 having a flared annular mounting 15 which attaches to a common optical connector such as a "C" mount connector. This flared annular mounting 15 resembles the eyepiece of a standard endoscope. The coupler 10 further includes a second end 13 having an endoscope mount 18 characterized by a substantially cylindrical section which may be configured to match the particular type of endoscope used. As best seen in FIGS. 3 and 6, in a preferred embodiment, the endoscope mount 18 may include an interior cylindrical wall 20 for receiving a standard endoscope having an annular eyepiece EP. Between the annular mounting 15 and endoscope mount 18 is a neck portion 16. Flared annular mounting 15 is inserted within a hole located at the distal end 26 of the drape 12 such that the hole surrounds neck portion 16. A sealing means 28 such as surgical tape may be used to seal the distal end 26 against the neck portion 16, thus providing a sterile barrier between the first and second ends of the coupler 10. Sealing and bonding of the drape 12 to the coupler 10 may also be done by a variety of methods, including adhesives, shrink-wrap or double-faced adhesive strips.

Sterile drape 12 may include folds 17 in order to reduce the size of the drape for storage prior to use. As shown in FIG. 2, folds 17 may be telescopic wherein consecutive drape sections are folded on top of one another, or alternatively folds 17 may be folded in a roll configuration (not shown) like a condom. If folds 17 are telescopic, pull tab 14 may be provided in order to extend the drape for use. As seen in FIG. 3, the primary purpose of coupler 10 is to provide an optical pathway and sterile barrier between a sterile endoscope E and an unsterile camera setup including video camera VC and optical connector OC. Accordingly, interior passageway 30 is provided to allow light to be transmitted from the endoscope E to the video camera VC. To maintain sterility, optically clear window 32 is provided which allows the passage of light and provides a sterile barrier between the video camera VC and endoscope E. As best seen in FIGS. 3 and 6, for use of the coupler 10 with an endoscope E of the type having a conventional eyepiece EP, the eyepiece EP is inserted within endoscope mount 18 such that the eyepiece EP is pressed flush against interior wall 34 and window 32. Retaining screws 22 may then be used to secure the eyepiece EP. Alternatively, endoscope mount 18 could be configured like mount portion M of optical connector OC in order to receive the standard eyepiece EP of an endoscope. Other methods of securing the mount 18 to the endoscope are possible within the intended scope of this disclosure as will be discussed below.

In addition to the preferred embodiment of endoscope mount 18 as illustrated in FIGS. 2 through 7, endoscope mount 18 may be configured to match any number of differing types of endoscopes. For example, as shown in FIG. 8, endoscope mount 18 may include interior threads 36 for which to receive exterior threads ET of endoscope $E_1$. In another embodiment, as shown in FIG. 9, endoscope mount 18 may include a generally circular recess 38 for which to receive ball detent BD of endoscope $E_2$. In yet another embodiment, as shown in FIG. 10, endoscope mount 18 may include an O-ring 40 for which to receive an endoscope $E_3$ that has a compression fitting CF.

The coupler 10 can be made of a suitable plastic or metal material which is sterilizable by various methods such as gas sterilization or gamma radiation and thus is made completely sterile. A suitable material for the coupler may be polycarbonite or PETG, or possibly acrylic or styrene. Similarly, the sterile drape 12 may be made out of a material such as polyethylene preferably from 1 to 6 mils in thickness, that is sterilizable also making the drape completely sterile.

In operation, as best seen in FIGS. 4–6, video camera VC and optical connector OC are inserted within the proximal end of sterile drape 12. Mounting portion M of optical connector OC is coupled to flared annular mounting 15 of coupler 10. Video camera VC may then be attached to connector OC. Sterile drape 12 is then pulled back over the optical connector OC, video camera VC and its trailing cables thus providing a sterile covering isolating the unsterile camera setup from the sterile operating environment. Sterile endoscope E may then be coupled with endoscope mount 18 of coupler 10. The endoscope E may be secured by means of retaining screws 22 or other appropriate securing means. If it is desired to use a different type of endoscope having differing optical qualities, retaining screws 22 are simply released and endoscope E is removed from mount 18. A new endoscope may then be introduced wherein sterility is maintained during the change in endoscopes. After use, the optical connector OC and endoscope E are disconnected from the coupler 10, and the drape 12 and coupler 10 are thrown away.

With this apparatus and method, a standard surgical camera and optical connector can be used which does not need to be sterilized through heating, soaking, or other sterilizing procedures and in which a number of endoscopes may be used with the same camera setup. The advantages of sterility and interchangeability of endoscopes makes this invention attractive to medical clinics and hospitals who often times cannot afford other endoscopic systems which, in order to maintain sterility, are much more complex and more difficult to use.

As discussed above in the prior art, an endoscope is typically attached to the optical connector which meant that in order for an endoscope to be placed in use, the sterile eyepiece of the endoscope had to be inserted within the drape and then directly attached to the unsterile optical connector. During this process, contamination is allowed to freely travel from the inside of the drape where the unsterile camera and optical connector are positioned, to the outside sterile environment of the operating room by means of the hole located in the distal end of the drape. Thus, according to the device and method of the invention disclosed herein, by isolating the first end of the coupler within the drape, sterility may be maintained when attaching the endoscope to the coupler and for subsequent acts of changing endoscopes with the same camera setup.

This invention has been described in detail with reference to a particular embodiment thereof, but it will be understood that various other modifications can be affected within the spirit and scope of the invention.

I claim:

1. An apparatus for optically coupling a sterile endoscope to an unsterile optical connector and enclosing an unsterile connector mounted to an unsterile camera having trailing cables in a sterile enclosure for use of an unsterile camera in a sterile surgical environment, said apparatus comprising:

a sterile coupler having a first end including a flared annular mounting for connection to an unsterile optical connector and having a second end including a mounting means for connection to a sterile endoscope, said coupler further having an optical path through which an image may be transmitted from an endoscope to a camera;

an optically clear window mounted transversely in said optical path;

a sterile drape having a open distal end positionable over said first end of said coupler and having a proximal end extendable over an unsterile optical connector, a camera and its trailing cables; and means for sealing said distal end of said drape to said coupler whereby said first end of said coupler is isolated from the sterile surgical environment outside said drape.

2. An apparatus, as claimed in claim 1, wherein said optical that includes:

an interior passageway formed within said coupler extending from said first end through said second and thereof and having said optically clear window mounted thereacross.

3. An apparatus, as claimed in claim 1, wherein said sterile barrier includes:

an optically clear window mounted transversely in said optical path.

4. An apparatus, as claimed in claim 1, wherein said mounting means includes:

a substantially cylindrical section having a smooth interior surface for receiving an endoscope of the type having an annular eyepiece; and securing means on said mounting means for releasably attaching said mounting means to an endoscope.

5. An apparatus, as claimed in claim 1, wherein said securing means includes at least one screw.

6. An apparatus, as claimed in claim 1, wherein said mounting means includes:
a substantially cylindrical section having an interior surface including threads for releasably attaching said mounting means to an endoscope of the type having an exterior threaded end.

7. An apparatus, as claimed in claim 1, wherein said mounting means includes:
a substantially cylindrical section having a generally circular recess for releasably attaching said mounting means to an endoscope of the type having a spring ball detent.

8. An apparatus, as claimed in claim 1, wherein said mounting means includes:
a substantially cylindrical section having an O-ring attached thereto for releasably attaching said mounting means to an endoscope of the type having a compression fitting.

9. An apparatus for coupling a sterile endoscope to an unsterile optional connector and camera wherein an unsterile connector and camera are shielded from a sterile surgical environment, said apparatus comprising:
a means for coupling an unsterile optical connector and camera to a sterile endoscope, said coupling means including a first end for connection to an unsterile optical connector and a second end for connection to a sterile endoscope;
an optical passageway extending from said first end of said coupling means through said second end of said coupling means enabling an image to be transmitted from the endoscope to the camera;
a window means positionable between said first and second ends of said coupling means, said window means providing a sterile barrier therebetween;
a sterile drape having an open distal end positionable over said first end of said coupler and having a proximal end extendable over an unsterile optical connector and camera; and
means sealing said open distal end of said sterile drape to said coupling means between said ends thereof to form a fluid and airtight seal.

10. Apparatus, as claimed in claim 9, wherein said first end of said coupling means includes:
a proximal mounting means for releasable attachment of said first end of said coupling means to the optical connector.

11. Apparatus, as claimed in claim 9, wherein said second end of said coupling means includes:
a distal mounting means for releasable attachment of said second end of said coupling means to the sterile endoscope.

12. Apparatus, as claimed in claim 9, further including:
a neck portion positioned between said first and said second ends of said coupling means.

13. A method of coupling an unsterile camera setup including an optical connector and camera to a sterile endoscope wherein differing endoscopes may be freely interchanged without compromising the sterility of a surgical environment, said method comprising the steps of:
providing a sterile coupler having a first end attachable to an unsterile optical connector and a second end attachable to a sterile endoscope and further having an optical path therethrough from the first end to the second end with an optically clear window mounted transversely in the optical path;
providing a sterile drape having an open distal end positionable over the first end of the coupler and having a proximal end extendable over a camera setup;
sealing the distal end of the drape around the first end of the coupler thereby providing a sterile seal wherein the first end of the coupler is sealed within the drape and the second end of the coupler is exposed to the sterile surgical environment;
inserting an unsterile optical connector attachable to an unsterile camera within the proximal end of the drape;
attaching the unsterile optical connector to the first end of the coupler; and
attaching a sterile endoscope to the second end of the coupler.

14. A method of coupling an unsterile camera setup to a sterile endoscope wherein sterility is maintained and wherein differing endoscopes may be freely interchanged without compromising the sterility of a surgical environment, said method comprising the steps of:
providing a sterile coupler having a first end releasably attachable to an unsterile camera setup and a second end releasably attachable to a sterile endoscope;
providing a sterile drape having an open end positionable between the ends of the sterile coupler wherein the drape provides a first sterile barrier between exterior portions of the ends of the sterile coupler;
sealing the open end of the sterile drape between the ends of the sterile coupler;
providing a clear optical pathway within the sterile coupler wherein an image may be transmitted from the endoscope to the camera setup;
providing a window positionable within the sterile coupler along said optical pathway wherein a second sterile barrier is created between the interiors of the first and second ends of the sterile coupler;
attaching the first end of the sterile coupler to the camera setup; and
attaching the second end of the sterile coupler to the sterile endoscope.

* * * * *